(12) United States Patent
Soykan (10) Patent No.: US 8,057,466 B2
(45) Date of Patent: Nov. 15, 2011

(54) METHOD AND DEVICE TO FORM A SENSOR USING ISOLATED CARDIOMYOCYTES

(75) Inventor: Orhan Soykan, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1111 days.

(21) Appl. No.: 11/515,568

(22) Filed: Sep. 5, 2006

(65) Prior Publication Data

US 2007/0010784 A1   Jan. 11, 2007

Related U.S. Application Data

(63) Continuation of application No. 10/409,537, filed on Apr. 8, 2003, now Pat. No. 7,310,545.

(60) Provisional application No. 60/372,218, filed on Apr. 12, 2002.

(51) Int. Cl.
*A61B 18/18* (2006.01)

(52) U.S. Cl. .................................................. 606/33

(58) Field of Classification Search ............... 606/33
See application file for complete search history.

(56) References Cited

U.S. PATENT DOCUMENTS

| | | | | |
|---|---|---|---|---|
| 5,403,306 | A * | 4/1995 | Edwards et al. | 606/3 |
| 5,586,981 | A * | 12/1996 | Hu | 606/9 |
| 6,254,600 | B1 * | 7/2001 | Willink et al. | 606/41 |
| 6,432,067 | B1 * | 8/2002 | Martin et al. | 601/2 |
| 6,626,855 | B1 * | 9/2003 | Weng et al. | 601/3 |
| 7,344,533 | B2 * | 3/2008 | Pearson et al. | 606/41 |

OTHER PUBLICATIONS

Christini, et al., Direct biologically based biosensing of dynamic physiological function, American Journal Physiological Heart Circ. Physiol 280: H2006-H2010, 2001.
Haruyama et al., A biosensing system based on extracellular potential recording of ligand-gated ion channel function overexpressed in insect cells, Analytical Chemistry, 75(4), 2003.
Miake, et al., Biological pacemaker created by gene transfer, Nature Publishing Group; 419:132-133, 2002.
Qu, et al., Expression and Function of a Biologcal Pacemaker in Canine Heart, Circulation, 107:1106-1109, 2003.
Subrahmanyam et al., Application of natural receptors in sensors and assays, Analytical Chemistry, 74(16):3942-3951, 2002.
Tang, et al., Genetically engineered biologically based hemostatic bioassay, Annals of Biomedical Engineering, 31:159-162, 2003.

* cited by examiner

*Primary Examiner* — Lee Cohen
(74) *Attorney, Agent, or Firm* — Michael C. Soldner

(57) ABSTRACT

A method and device are described to form a sensor using a cardiomyocyte by advancing a catheter into the tissue of interest, cardiac in the preferred embodiment, and using the catheter to ablate a cone- or a dome-shaped region to form an electrically isolated section of tissue. An electrode is later fixed to the region encompassed by the dome-shaped area of tissue and used to detect the electrophysiological activity of this electrically independent cluster of cells. These cells combined with the electrode and a detection circuitry will form a cell-based sensor to monitor the effects of the anti-arrhythmic drugs in the circulation. The inventive device includes an ablation catheter and a sensing lead. Catheter is a hollow conductor which used to carry RF power from the external generator to the myocardium and to form a cone-shaped ablation zone to electrically isolate a part of myocardium from the rest. Sensing lead is a conductor that carries electrical signals from the isolated myocardium back to the implanted monitoring device. Implantable device is the main unit for processing the signals coming back from the sensing lead.

23 Claims, 6 Drawing Sheets

Catheter designed for controlled tissue necrosis for the attachment of the sensing electrode.

FIG. 1

Catheter designed for controlled tissue necrosis for the attachment of the sensing electrode.

FIG. 2

Electromagnetic waves traveling in a waveguide reach to the load end, and disperse into the external media.

FIG. 3

Steerable Beam Antenna used to direct the electromagnetic beams toward a desired direction around the antenna.

FIG. 4

Envisioned system after deployment.

FIG. 5

Expected response from the leads 4 and 11 in Figure 4.
(A) Rate change due to pharmaceutical input
(B) Rate change due to physiological input, such as exercise

FIG. 6

Measurement of the Refractory Period

METHOD AND DEVICE TO FORM A SENSOR USING ISOLATED CARDIOMYOCYTES

This application is a continuation of U.S. application Ser. No. 10/409,537, filed on Apr. 8, 2003, which issued as U.S. Pat. No. 7,310,545 on Dec. 18, 2007. The entire contents of U.S. application Ser. No. 10/409,537 are incorporated herein by reference. U.S. application Ser. No. 10/409,537 claimed the benefit of U.S. Provisional Application No. 60/372,218, filed on Apr. 12, 2002.

BACKGROUND OF THE INVENTION

1. Field of the Invention

The present invention relates generally to drug concentration sensors. More specifically, the present invention relates to a method and device to form a sensor using isolated cardiomyocytes. The sensor of the present invention is formed from endogenous tissue using an ablation catheter to ablate a cone- or dome-shaped region of tissue in the heart to form an electrically isolated tissue section of cardiomyocytes. An electrode is fixed to the region of isolated tissue and is used to detect the electrophysiological activity of this electrically independent cluster of cells. These cells combined with the electrode and a detection circuitry will form a cell based sensor to monitor the effects of the anti-arrhythmic drugs in the circulation.

2. Background of the Invention

It can be appreciated that drug concentration sensors have been in use for years. Typically, drug concentration sensors are comprised of point of care measurement systems where the concentration of drugs in the circulation can be measured from blood drawn from patients.

The main problem with conventional drug concentration sensors is that they do not provide continuous data unless the sensor is implanted. Sensors created from cells native to the body would not suffer from such problems. Edelberg et al. [Am J Physiol Heart Circ Physiol 280: H2006-H2010, 2001] demonstrated the feasibility of using cardiac cells to sense drug concentrations by implanting donor cardiomyocytes into a non-cardiac site in a recipient animal and monitoring them electrophysiologically while administering pharmaceutical agents. The present invention takes the concept one step further by turning it into a catheter and lead based procedure and eliminates the need for a donor tissue, although donor cells or tissue can be used with the present invention.

The present invention also provides a solution to the problem of patient compliance in taking prescribed medications. Most anti-arrhythmic drugs are prescribed to patients with chronic conditions such as atrial fibrillation and ventricular tachycardia. However, a general problem is patient compliance in taking their medical prescription. If the implantable device could monitor the effect of the drug on the cardiac rhythm, this information could be used for closed loop drug delivery. Closed loop delivery of the drug with integration of the sensors of the present invention also provides improved avenues for more effective use and delivery of drug.

A further improvement of the present invention is in providing a demand based delivery system based on functional measurements from the isolated cardiomyocytes. Most medications are taken at routine times during the day. Because schedule-based delivery only estimates the actual need, often the effective concentration of the drug are less than optimal. A closed loop system utilizing the isolated tissue sensor provides a means to monitor the body's direct requirements for the drug, and then delivers the proper dose on a demand basis.

Another problem with conventional drug concentration sensors is that artificial sensors utilizing synthetic enzymes require periodic replacement of the enzyme that they use, limiting the useful life of the sensor. Sensors using the natural cells of the body would not require the periodic maintenance and the resupply of conventional sensors, making them very suitable for implantable applications.

While sensors described in the prior art may be suitable for the particular purpose that they address, they generally are not as suitable for long-term implantation. Most implantable sensors suffer from problems related to stability and sensor encapsulation. Cells native to the body would not suffer from such problems.

In these respects, the method and device to form a sensor using a cardiomyocyte according to the present invention substantially depart from the conventional concepts and designs of the prior art, and in so doing provide an apparatus primarily developed for such a purpose. In order to create a sensor of the present invention, typically a catheter is advanced into the tissue of interest, cardiac in the preferred embodiment, and is then used to ablate a cone- or a dome-shaped region in the tissue to form an electrically isolated section of tissue. An electrode is later fixed to the region encompassed by the dome-shaped area of tissue and used to detect the electrophysiological activity of this electrically independent cluster of cells. These cells combined with the electrode and a detection circuitry can be used to form a cell-based sensor to monitor the effects of the anti-arrhythmic drugs in the circulation without the chronotopic influence existing on the remainder of the myocardial cells.

SUMMARY OF THE INVENTION

In view of the foregoing disadvantages inherent in the known types of drug concentration sensors now present in the prior art, the present invention provides a new method and device to form a sensor using an isolated region of cells. In a preferred embodiment the isolated sensing region is composed of a region of electrically isolated cardiomyocytes. Construction of the isolated region of cells within the targeted tissue is typically obtained by advancing an ablation catheter to the tissue of interest, which is then used to ablate a cone- or a dome-shaped region to form an electrically isolated section of tissue. An electrode is later fixed to the region encompassed by the dome and used to detect the electrophysiological activity of this electrically independent cluster of cells. These cells combined with the electrode and a detection circuitry can be used as a cell-based sensor to monitor the effects of the anti-arrhythmic drugs in the circulation without the chronotopic influence existing on the remainder of the cells.

In one embodiment, formation of the natural sensor requires an ablation catheter and at least one sensing lead. The ablation catheter is a hollow conductor that carries radio frequency (RF) power from the external generator to form a cone-shaped ablation zone to electrically isolate a group of cells from the rest of the tissue. The sensing lead is a conductor that carries electrical signals from the isolated cells in the tissue back to the implanted monitoring device. The implantable device is the main unit for processing the signals coming back from the sensing lead.

In one preferred embodiment the present invention provides a sensor system formed from isolated cardiomyocytes. These isolated cells combined with an electrode and detection circuits form the basis of the cell-based sensors. Another preferred embodiment is to provide a method and device to form the group of isolated cardiomyocytes in the tissue wherein an ablation catheter is advanced to the heart and the catheter is used to ablate a cone- or a dome-shaped region to form an electrically isolated section of tissue. An electrode is later fixed to the region encompassed by the dome-shaped area of tissue and used to detect the electrophysiological activity of this electrically independent cluster of cells. These cells combined with the electrode and a detection circuitry form a cell-based sensor. Such a sensor can be used to monitor the effects of the anti-arrhythmic drugs in the circulation.

Another object of the invention is to provide a method and device to monitor the functional effect of various anti-arrhythmic drugs in the blood. For instance, cardiomyocytes respond to pharmaceuticals by changing their resting rate of depolarization, making them a natural sensor to detect the levels of anti-arrhythmic drugs in the circulation. However, cardiac cells are electrically connected to each other and are under the influence of multiple physiologic signals. This invention describes a method to electrically isolate a small cluster of cells from the remainder of the cardiac muscle to form a sensor that primarily responds to drugs in the coronary circulation, with minimal chronotropic interference. Another object of the invention is to provide a method and device to form a sensor using isolated tissue cells, or another type of cell, that can be used separately or in combination as a monitoring tool, to isolate and measure the effects of drugs, and eventually adjust the delivery regimen. Preferably the exogenous cell used in the sensor contributes measurable electrophysiological characteristics. Exogenous cells used as part of sensor should be immuno-compatible with the host. Exogenous cells can be used in isolation or in combination with isolated cells of the natural tissue.

Another object of the invention is to provide a method and device to form a sensor using isolated myocardial cells, or other types of cells that are electrically isolated from the remainder of the cells in the organ tissue, to form the cell-based sensor.

Another object of the invention is to provide a method and device to form a sensor using an ablation methodology to electrically isolate the cells in the organ tissue. In one embodiment, the present invention provides a method and device to form a sensor using a cardiomyocyte that utilizes the concept of steerable beam antenna (phased antenna arrays) to form custom shaped ablation zones and electrically isolated tissue segments. In yet other embodiment, chemical, cryoablation, biological ablation, and mechanical ablation can be envisioned.

Other objects and advantages of the present invention will become obvious to the reader. It is intended that these objects and advantages are within the scope of the present invention In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and advantages of the present invention will become fully appreciated as the same becomes better understood when considered in conjunction with the accompanying drawings, in which like reference characters designate the same or similar parts throughout the several views, and wherein.

DETAILED DESCRIPTION

The present invention describes the formation and use of electrically isolated cells to form part of a sensor. It should be understood that the isolated cells may be formed from part of the existing tissue, and, therefore the term isolated cell sensor, isolated tissue sensor, and isolate cell/tissue sensor, and the like, refer to the constructed cells wherein the utilized cells have been electrically isolated by the techniques described herein.

In the drawings similar reference characters denote similar elements throughout the several views. The attached figures illustrate a method and device to form a sensor using a cardiomyocyte, which comprises an ablation catheter and a sensing lead. Catheter 1 is a hollow conductor that carries RF power from the external generator to the myocardium 2 to form a cone-shaped ablation zone 3 to electrically isolate a part of myocardium 5 from the rest of the tissue. Sensing lead 4 is a conductor that carries electrical signals from the isolated myocardium 5 back to the implanted monitoring device 6. Implantable device 6 is the main unit for processing the signals coming back from the sensing lead.

Figure 3:
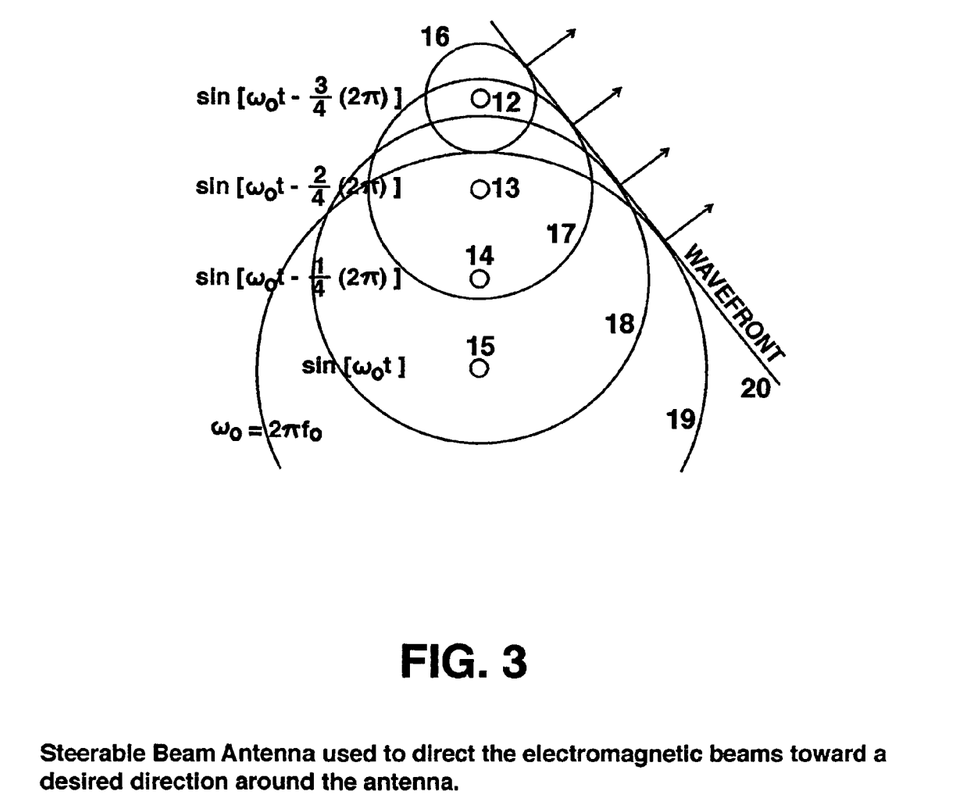
FIG. 3 is a diagram of a Steerable Beam Antenna used to direct the electromagnetic beams.

The catheter used can be, as shown, a hollow catheter 1 with walls 7 and 8. The catheter carries the high frequency electromagnetic waves between its walls. It is preferred that both the inner wall 7 and the outer wall 8 are formed by conductors, such as metals, metal coated polymers or conductive polymers. The space between the conductors 9 are air-filled and sealed at both ends with dielectric materials to keep the fluids from seeping in, but allowing the passage of the electromagnetic waves. Using a stylet, the catheter 1 can be positioned within the ventricular cavity, against a healthy region of the myocardium 2. The stylet is later removed while keeping the catheter 1 in place, and the proximal end of the catheter 1 is connected to a high frequency signal generator. The tip of the electrode that is in contact with the myocardium 2 is shown schematically in FIG. 3, optionally containing sensing electrode 4, which would be introduced later on. Electromagnetic waves produced by the generator travel between the walls 7 and 8 forming the shell of the catheter 1 and reaching to the distal end. Before the waveguide formed by walls 7 and 8 terminates at the tissue, catheter 1 splits into multiple branches, shown as four different bands at the end of the catheter 1. Path lengths for these branches are calculated to provide the desired transmission delay, For example, the phase shift needed to form a phased array to create penetrating waves into the tissue are shown turned toward the central axis of the catheter 1. This would expose a cone-shaped region of the myocardium to the electromagnetic waves and ablate it. However, the isolated cells of the myocardium 5 not directly in the ablation path 3 will be spared, electrically isolating viable tissue from the rest of the myocardium.

Sensing lead 4 is a conductor that carries electrical signals from the isolated myocardium 5 back to the implanted monitoring device 6. Following ablation, the hollow lumen of the catheter 1 can be used to advance a sensing electrode 4 for attachment to the electrically isolated myocardial cells 5, preferably with an active fixation mechanism. Finally, the catheter 1 is removed, leaving the sensing electrode 4 in contact with the electrically isolated myocardium 5. The isolated cells and sensing electrode form the cell-based sensor. Sensing lead 4 could contain a single electrode and be configured in unipolar fashion, or could contain two electrodes and be configured in bipolar fashion. Furthermore, the cell-based sensor could have passive fixation using tines, or could contain active fixation to the myocardium 2 via screw-in process.

Figure 4:
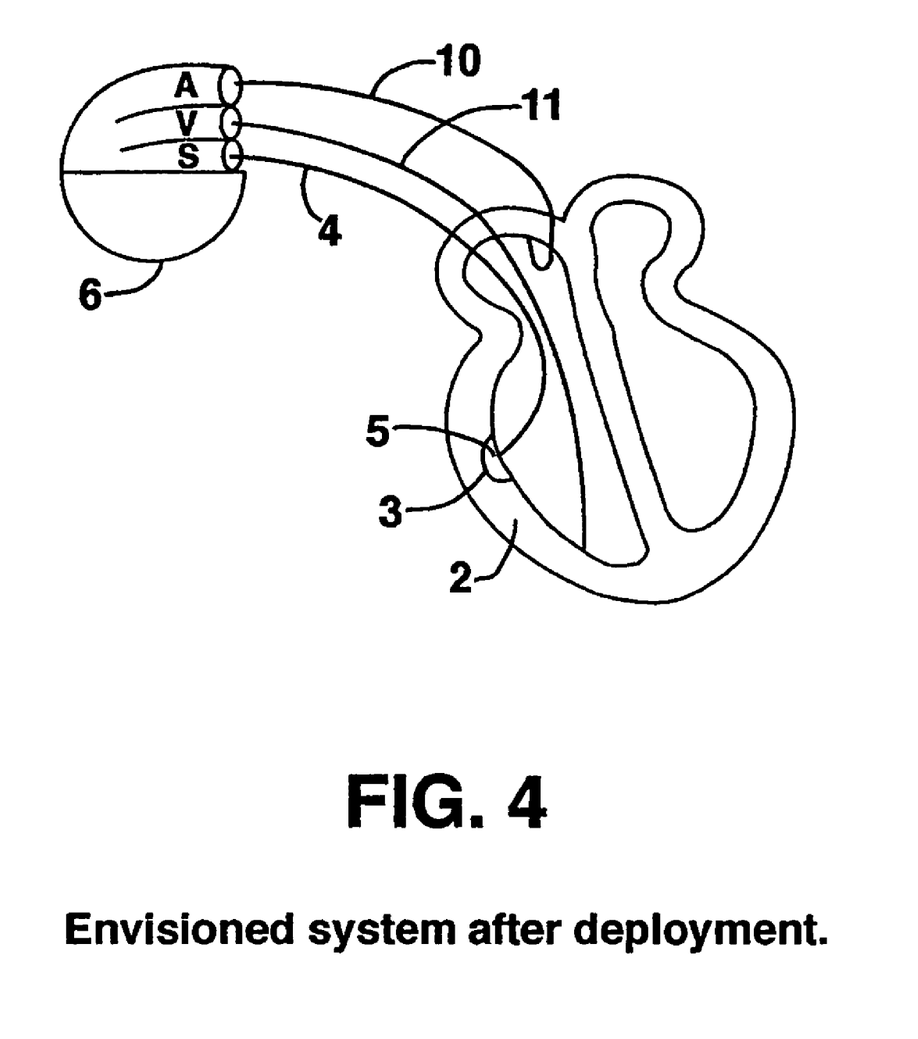
FIG. 4 is a diagram of the envisioned system after deployment.

Implantable device 6 is the main unit for processing the signals coming back from the sensing lead 4. An implantable device 6 with three ports is utilized to take advantage of the cell-based sensor. Atrial leads 10 and ventricular leads 11 are utilized in their usual fashion, e.g., for use in sensing intrinsic activities of the atria and ventricles, and for pacing. The third electrode 4, labeled with letter "S" in FIG. 4, is used to sense the electrophysiological activity of the tissue segment 5 electrically isolated from the rest of the myocardium 5. This isolated segment is not under the chronotropic influence of the rest of the myocardium 2, but still receives the pharmaceuticals from the coronary circulation. Hence, the implantable device 6 can detect the level of effects of drugs from the measured electrophysiologic activity of the isolated myocardium. Furthermore, the availability of the ventricular lead 11 will allow the elimination of the far field R-waves from the sensing signal. Such a device could be used for enhancing the monitoring capabilities of the implantable devices, and can also be used to provide feedback to an implantable drug pump. Implantable device 6 could be a pacemaker, a defibrillator, or a simple monitoring device. It could also be an implantable drug delivery device, or a combination of any of the above.

Figure 1:
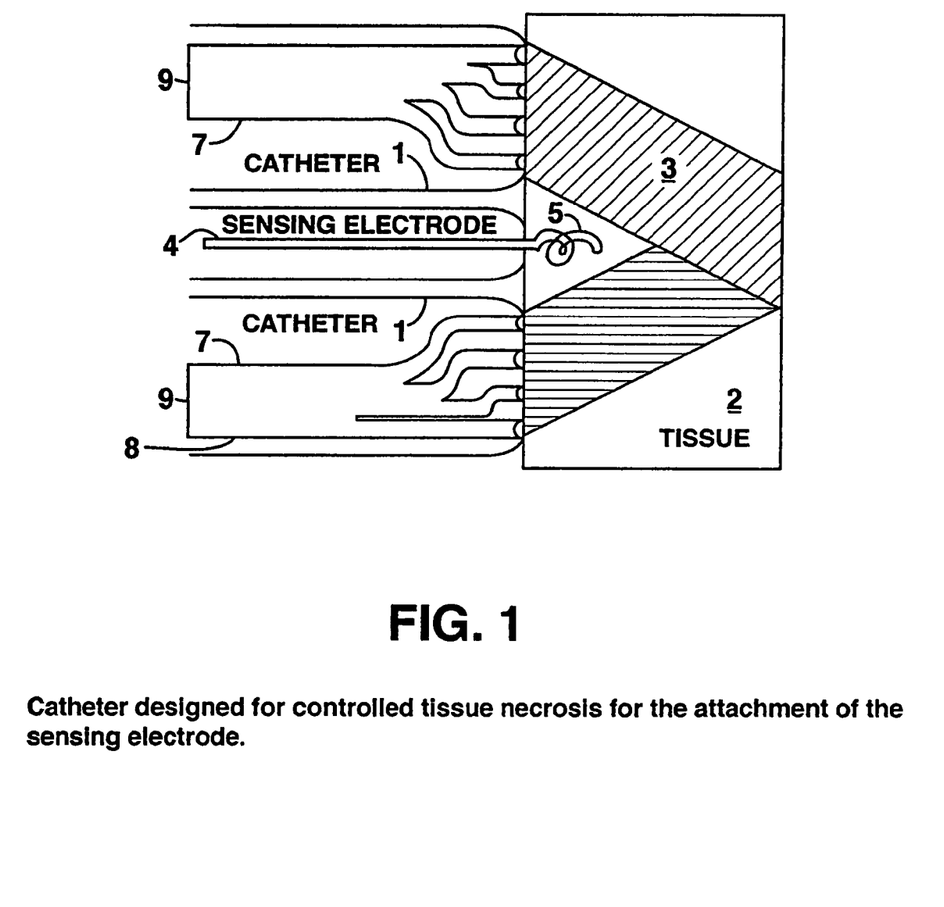
FIG. 1 is a diagram of the catheter designed for controlled tissue necrosis and attachment to the sensor.
Figure 2:
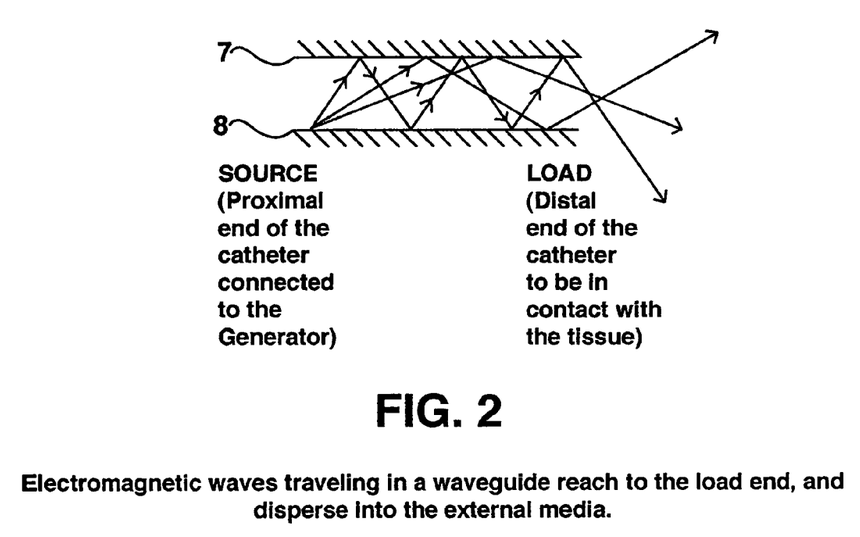
FIG. 2 is a diagram of electromagnetic waves traveling in a waveguide.

The purpose of catheter ablation is to destroy myocardial tissue 3 by delivering electrical energy using electrodes of a catheter 1 placed on the myocardium 2. Radio frequency (RF) energy delivered by the electrodes is provided by an external generator and destroys the tissue by controlled heat production. RF energy is delivered between the distal (tip) electrode of the catheter 1 and an indifferent electrode placed elsewhere on the patient's body, usually as an external pad on the skin of the patient's thigh. In the human body, electrical conduction is achieved by ions, which are too large to move back and fourth at the radio frequencies. Instead, RF energy causes resistive heating of the cells surrounding the tip electrode of the catheter 1. Once tissue temperature exceeds 50° C., irreversible cellular damage and tissue death occurs. Newly formed scar tissue is not able to conduct the electrical impulses of the myocardium. Electromagnetic waves travel in free space and in air without requiring a conductive medium. Since air and free space do not conduct electricity, there is no power dissipation in either medium (recall that $P=V^2/R$, where $R=\infty$). In the tissue, however, the resistance is not infinite; therefore, the power is dissipated in the form of heat. As a result, wave amplitude would decrease once the electromagnetic waves leave the air and enter the tissue. Electromagnetic waves could be guided and directed in a preferred direction by the use of special structures called waveguides which could be formed by the inner 7 and outer walls 8 of the hollow catheter 1. Waveguides can be constructed using conductors, such as metals, or dielectrics like glass as in the case of optical fibers, or combinations, as in the case of micro-strip lines. Transmission of waves within these guides can be explained as multiple reflections from the walls 7 and 8 of the waveguide. Electromagnetic waves travel through the cavity of the waveguide until they reach the load end, which is the end opposite to the source end connected to the generator. Waves reaching the load end would be freed from the restriction imposed by the walls 7 and 8 of the waveguide and would disperse into the external medium. This condition is shown on FIG. 1. As waveguides focus the electromagnetic waves inside them toward the direction of the waveguide, steerable beam antennas (phased array antennas and linear antenna arrays) influence the direction of the waves upon the termination of the guide. Principle of such an arrangement is shown in FIG. 2. In one implementation, four sources 12, 13, 14 and 15 simultaneously transmit electromagnetic waves at the same frequency, $f_0$, but with some phase shift, or time delay. In the implementation shown in FIG. 2, the transmitter 15 transmits electromagnetic waves with no delay, allowing the waves emanating from this transmitter to travel farther in space before the other transmitters 12, 13 and 14 begin to send out the same wave. This is indicated by circle 19 representing the traveling wave, centered on the bottom transmitter, having the largest radius. Remaining transmitters 12, 13, and 14 transmit with linearly increasing delays, as shown with waves 16, 17 and 18, which traveled shorter distances and therefore have reduced radii. This arrangement allows the formation of a wavefront 20 where the direction of travel for the beam is controlled by adjusting the phase-shift (time delay) between the transmitters 12, 13, 14 and 15. Although the above description included a method where a single external RF source was used to feed RF signals to the catheter 1 which in turn generated the phase shifted signals at the distal end for phased array, it is also possible to generate the phase shifted signals at the source and carry them to the distal end using separate waveguides. It is also possible to place the RF oscillators at the distal end and power them from an external source placed at the proximal end.

One operation of the present invention can be summarized as follows: A suitable portion of the myocardium 2 is identified as a candidate region for the formation of the cell-based sensor. Its suitability is confirmed by electrogram to assure that the region contains viable tissue and ablation around the region would not cause re-entrant arrhythmias. Catheter 1 is advanced to the position and RF power is applied to form the cone-shaped isolation zone 3. Afterwards, the sensing electrode 4 is attached to the isolated myocardium 5 and the isolation is confirmed with the a synchronous rates of depolarizations observed from the ventricular 11 and the sensing leads 4 shown on FIG. 3. Atrial 10 and ventricular leads 11, as well as the sensing lead 4, are all connected to the implantable device 6. Under ambulatory conditions, implantable device 6 receives electrical signals from both the ventricular 11 and sensing leads 4. The rate of depolarization measured from the ventricular lead 11 would be controlled by the chronotropic influence of the cardiovascular physiology as well as the administered pharmaceuticals. Signals from the isolated myocardium 5 would show the influence of the pharmaceuticals primarily, and would indicate the independent effects of the anti-arrhythmic drugs on the cardiomyocytes.

The foregoing description is considered as illustrative of the principles of the invention. Numerous modifications and changes will be readily apparent to one skilled in the art.

EXAMPLES

An example problem that the invention is designed to solve is presented: Many anti-arrhythmic drugs have a very narrow range of effectiveness. For example, effective plasma concentration of quinidine is 3-6 µg/mL. It is eliminated by the liver, and its half life in the blood is 5-9 hours. Patients take 300-600 mg every 6 hours to maintain the drug within the effective range, which causes the concentrations in the blood to swing from the maximum to the minimum of this range (3-6 µg/mL) between administrations. If the patient delays the administration, or forgets it altogether, then the drug concentration in blood will fall below the therapeutic range, and the patient would be vulnerable to life-threatening arrhythmias. A sensor which can sense the anti-arrhythmic effects of drugs in the blood, such as the one described in this invention, would warn the patient or trigger an implantable drug pump to release additional drugs, quinidine in this case, into the bloodstream.

An example sensor system was formed by Edelberg et al., where hearts from donor mice were implanted into the ears of recipient mice. In this experiment, endogenous and exogenous hearts were not in electrical contact. When propranolol, a β-blocker, was administered, R-R interval (time between the two successive QRS complexes of the ECG, measured to determine the duration of the cardiac cycle) of the exogenous heart was more than doubled in three minutes, where the increase in the R-R interval of the endogenous heart was less than 20 percent, showing that the isolated cardiomyocytes in the ear were much more sensitive to the drugs in the circulation. Since the isolated myocytes were not influenced by other factors such as filling pressures and arterial loads, the changes in the electrical behavior of the isolated cells would be more specific. A change in the endogenous heart rate would not be specific to the drug administration, whereas a change in the rate of isolated heart cells would be specific to the drugs in the blood. The present invention utilities this fact in the design of the present invention.

Implementation 1

Sensor Formation:

Cells in the electrically isolated region of the myocardium can be converted into rhythmically depolarizing cells by molecular interventions. For example, it was shown by E. Marbán et al (Nature, 12 Sep. 2002) that the molecular suppression of Kir2 channel unleashes pacemaker activity in ventricular myocytes. Conversion of atrial myocytes into oscillators was also demonstrated by M. Rosen et al (Circ, February 2003) where the administration of AdV-HCN2 initiated SA nodal activity in canine left atrium.

Since the cells in this isolated region are not in electrical contact with the rest of the myocardium, their rhythmic behavior does not lead to arrhythmias. However, the cells in this region are not under any of the usual chronotropic input as the sinus-atrial (SA) node. Therefore, the isolated cells respond more specifically to the drugs which control the heart rate and the arrhythmias, but do not respond either to the changes in the systemic oxygen consumption or to the changes in total peripheral arterial resistance.

Figure 5:
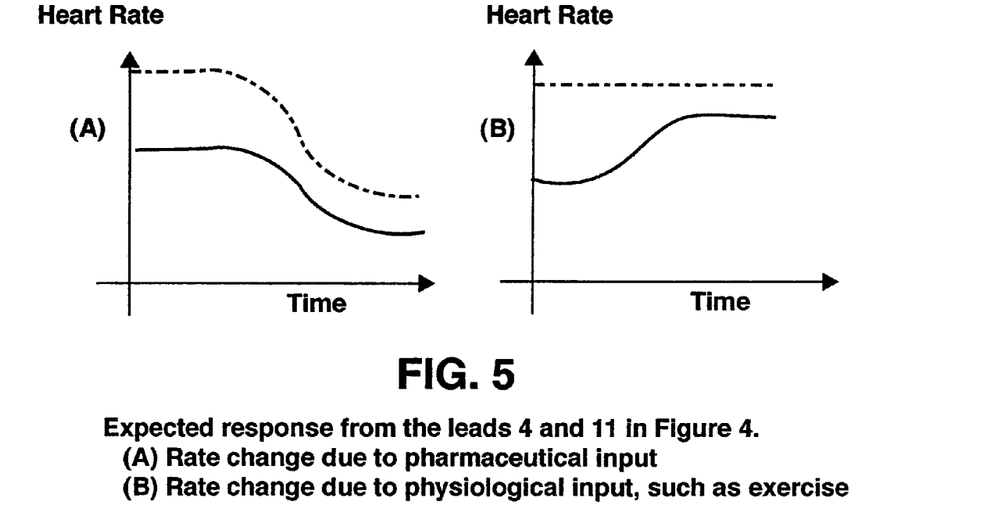
FIG. 5 is a diagram of the expected response from deployed sensing leads.

Above described sensor would show high specificity to drugs which block beta-adrenergic receptors, such as propranolol, timolol, metoprolol, etc. The rate observed from this region 5 as sensed by the lead 4, as shown in figure, would primarily correspond to the concentration of β-blockers in the bloodstream, while the rate sensed by the lead 11 in FIG. 4 would be affected by physiologic condition of the patient as well as pharmacological inputs. In FIG. 5, the solid line shows the rate of the ventricular myocardium being sensed from lead 11 and the dashed line shows the rate of the isolated region from lead 4 being sensed.

Implementation 2

Sensor Formation:

The electrically isolated region does not contain cells with intrinsic oscillatory behavior. Although these cell do not depolarize rhythmically, they would respond to electrical stimulation applied via lead 4 in FIG. 4. Amplitude of the electrical stimulation can be chosen such that it is sufficient to depolarize the isolated region 5 in FIG. 4, but not sufficient to conduct through the necrotic tissue (3) and excite the remaining myocardium (2).

Once the electrical stimulation amplitude and pulse-width is chosen as explained above, one can measure the refractory period at the isolated region. Two stimuli are delivered to the region in rapid succession (e.g. $\Delta T=150$ msec), and the evoked response is detected. If both stimuli capture and excite the isolated region, as evidenced by the presence of evoked response following each pulse, it would be concluded that the refractory period is shorter than $\Delta T$. In this case, $\Delta T$ will be reduced, and the procedure is repeated. If only the first pulse captures, then it can be assumed that the refractory period is longer than $\Delta T$, and the procedure will be repeated with a longer $\Delta T$.

Measurement of refractory period would indicate the concentration of sodium channel blockers such as quinidine, procainamide and diisopyramide, as well as potassium channel blockers such as bretylium and sotalol, as they directly alter the duration of the refractory period. The method described above for the measurement of the refractory period using two successive pulses is only applicable to the isolated region of the heart, since the paired pulses applied to the remaining myocardium (2) via the ventricular lead (11) could cause fibrillation and death of the patient if the second pulse were to coincide with the T-wave.

Figure 6:
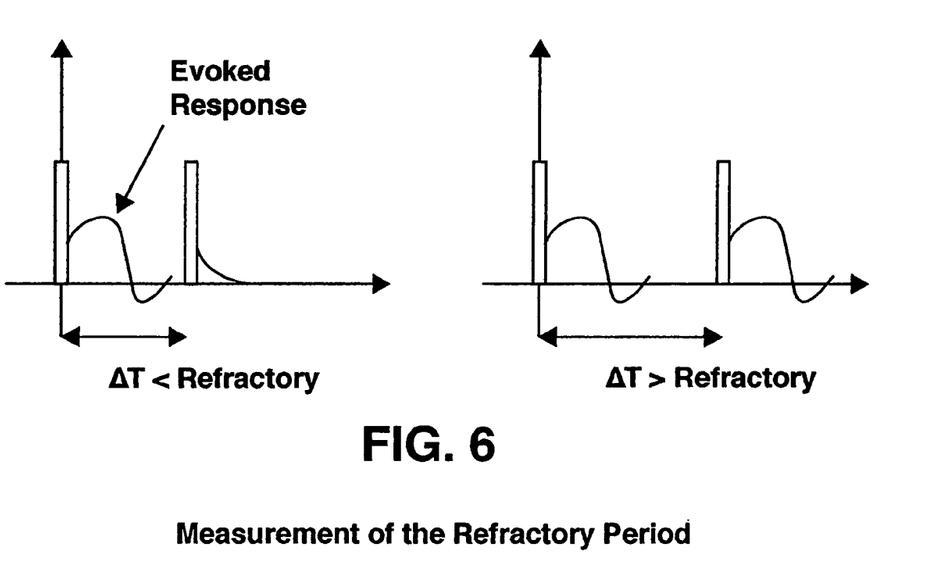
FIG. 6 is a diagram of timing of the stimulation pulses to measure the refractory period with and without electrical activity from isolated cardiomyocyte sensors.

FIG. 6 shows the expected response from the leads 4 and 11 of FIG. 4. In part (A) $\Delta T$<Refractory Period, as indicated by the lack of evoked response following the second stimulus, and (B) $\Delta T$>Refractory Period indicated by the presence of evoked responses following both stimulation pulses.

The invention claimed is:

1. A method comprising:
generating energy; and
directing the energy from a catheter to patient tissue along a cone-shaped ablation path, wherein at least a portion of the patient tissue within the cone-shaped ablation path is ablated, and patient tissue outside of the cone-shaped ablation path is not ablated, wherein directing the energy along the cone-shaped ablation path comprises introducing a phase delay to at least a portion of the energy, wherein introducing the phase delay to at least a portion of the energy comprises:
splitting the energy into a plurality of branches; and
introducing a phase delay to at least one branch of the plurality of branches to direct the energy along the cone-shaped ablation path, and wherein introducing a phase delay to at least one branch of the plurality of branches includes selecting a path length of the at least one branch to introduce the phase delay.

2. The method of claim 1, wherein the catheter includes a distal end and a proximal end, and introducing a phase delay to at least a portion of the energy comprises introducing the phase delay at the proximal end of the catheter.

3. The method of claim 1, wherein introducing a phase delay to at least a portion of the energy comprises generating phase shifted signals.

4. The method of claim 1, wherein directing the energy along a cone-shaped ablation path comprises directing the energy along the cone-shape ablation path with at least one waveguide carried by the catheter.

5. The method of claim 1, wherein the catheter includes a distal end and a proximal end, and wherein generating the energy comprises generating the energy at the distal end of the catheter.

6. The method of claim 1, wherein directing the energy along the cone-shaped ablation path comprises causing the energy to exit an end of the catheter in proximity to the patient tissue at an acute angle with respect to a radial axis of the catheter.

7. A method comprising:
generating energy; and
directing the energy from a catheter to patient tissue along a cone-shaped ablation path, wherein at least a portion of the patient tissue within the cone-shaped ablation path is ablated, and patient tissue outside of the cone-shaped ablation path is not ablated, wherein directing the energy along the cone-shaped ablation path comprises introducing a phase delay to at least a portion of the energy, wherein introducing the phase delay to at least a portion of the energy comprises:
splitting the energy into a plurality of branches; and
introducing a phase delay to at least one branch of the plurality of branches to direct the energy along the cone-shaped ablation path, wherein introducing a phase delay to at least one branch of the plurality of branches includes directing the energy via the at least one branch configured to have a length that corresponds to the phase delay.

8. A method comprising:
generating energy; and
directing the energy from a catheter to patient tissue along a cone-shaped ablation path, wherein at least a portion of the patient tissue within the cone-shaped ablation path is ablated, and patient tissue outside of the cone-shaped ablation path is not ablated, wherein directing the energy along the cone-shaped ablation path comprises introducing a phase delay to at least a portion of the energy, wherein introducing the phase delay to at least a portion of the energy comprises:
splitting the energy into a plurality of branches; and
introducing a phase delay to at least one branch of the plurality of branches to direct the energy along the cone-shaped ablation path, wherein introducing a phase delay to at least one branch of the plurality of branches further comprises:
introducing linearly increasing delays to the plurality of branches.

9. A method comprising:
generating energy; and
directing the energy from a catheter to patient tissue along a cone-shaped ablation path, wherein at least a portion of the patient tissue within the cone-shaped ablation path is ablated, and patient tissue outside of the cone-shaped ablation path is not ablated, wherein directing the energy along the cone-shaped ablation path comprises introducing a phase delay to at least a portion of the energy, wherein introducing the phase delay to at least a portion of the energy comprises:
splitting the energy into a plurality of branches; and
introducing a phase delay to at least one branch of the plurality of branches to direct the energy along the cone-shaped ablation path, wherein splitting the energy into a plurality of branches comprises directing the energy via a plurality of waveguide branches.

10. A method comprising:
generating energy; and
directing the energy from a catheter to patient tissue along a cone-shaped ablation path, wherein at least a portion of the patient tissue within the cone-shaped ablation path is ablated, and patient tissue outside of the cone-shaped ablation path is not ablated, wherein directing the energy along a cone-shape ablation path comprises:
directing the energy along the cone-shape ablation path with at least one waveguide carried by the catheter; and
directing the energy along the cone-shaped path via at least one steerable beam antennae positioned at an end of the at least one waveguide.

11. The method of claim 10, wherein directing the energy along the cone-shaped ablation path via at least one steerable beam antennae comprises directing the energy via at least one steerable beam antennae selected from the group consisting of:
a phased array antenna; and
a linear antenna array.

12. A device comprising:
a catheter configured to be introduced in proximity to patient tissue and coupled to a generator that generates energy, wherein the catheter directs the energy to patient tissue along a cone-shaped ablation path,
wherein at least a portion of the patient tissue within the cone-shaped ablation path is ablated, and patient tissue outside of the cone shaped ablation path is not ablated, wherein the catheter introduces a phase delay into a least a portion of the energy to direct the energy to the patient tissue along the cone-shaped ablation path, wherein the catheter splits the energy into a plurality of branches, and introduces the phase delay to at least one branch of the plurality of branches to direct the energy along the cone-shaped ablation path, and wherein the phase delay is introduced to the at least one branch by selection of a path length of the at least one branch.

13. The device of claim 12, wherein the catheter includes a distal end and a proximal end, and wherein the catheter is configured to introduce a phase delay at the proximal end of the catheter.

14. The device of claim 12, wherein the catheter includes at least one waveguide configured to direct the energy to patient tissue along a cone-shaped ablation path.

15. The device of claim 12, further comprising:
at least one steerable beam antenna carried by the catheter that directs the energy along the cone-shaped ablation path.

16. The device of claim 15, wherein the steerable beam antenna includes at least one antenna selected from the group consisting of:
a phased array antenna; and
a linear antenna array.

17. The device of claim 15, wherein the catheter includes a plurality of branches, and wherein the at least one steerable beam antenna carried is configured to introduce a phase delay to at least one branch of the plurality of branches.

18. The device of claim 12, wherein the catheter directs the energy to exit an end of the catheter at an acute angle with respect to a radial axis of the catheter.

19. A device comprising:
a catheter configured to be introduced in proximity to patient tissue and coupled to a generator that generates energy, wherein the catheter directs the energy to patient tissue along a cone-shaped ablation path, wherein at least a portion of the patient tissue within the cone-shaped ablation path is ablated, and patient tissue outside of the cone shaped ablation path is not ablated, wherein the catheter introduces a phase delay into a least a portion of the energy to direct the energy to the patient tissue along the cone-shaped ablation path, wherein the catheter splits the energy into a plurality of branches, and introduces the phase delay to at least one branch of the plurality of branches to direct the energy along the cone-shaped ablation path, wherein the at least one branch is configured to have a length that corresponds to the phase delay.

20. A device comprising:

a catheter configured to be introduced in proximity to patient tissue and coupled to a generator that generates energy, wherein the catheter directs the energy to patient tissue along a cone-shaped ablation path, wherein at least a portion of the patient tissue within the cone-shaped ablation path is ablated, and patient tissue outside of the cone shaped ablation path is not ablated, wherein the catheter introduces a phase delay into a least a portion of the energy to direct the energy to the patient tissue along the cone-shaped ablation path, wherein the catheter splits the energy into a plurality of branches, and introduces the phase delay to at least one branch of the plurality of branches to direct the energy along the cone-shaped ablation path, wherein the plurality of branches introduce linearly increasing delays.

21. A device comprising:

a catheter configured to be introduced in proximity to patient tissue and coupled to a generator that generates energy, wherein the catheter directs the energy to patient tissue along a cone-shaped ablation path, wherein at least a portion of the patient tissue within the cone-shaped ablation path is ablated, and patient tissue outside of the cone shaped ablation path is not ablated, wherein the catheter introduces a phase delay into a least a portion of the energy to direct the energy to the patient tissue along the cone-shaped ablation path, wherein the catheter splits the energy into a plurality of branches, and introduces the phase delay to at least one branch of the plurality of branches to direct the energy along the cone-shaped ablation path, wherein the plurality of branches comprise a plurality of waveguide branches.

22. A device comprising:

a catheter configured to be introduced in proximity to patient tissue and coupled to a generator that generates energy, wherein the catheter directs the energy to patient tissue along a cone-shaped ablation path, wherein at least a portion of the patient tissue within the cone-shaped ablation path is ablated, and patient tissue outside of the cone shaped ablation path is not ablated, wherein the catheter includes at least one waveguide configured to direct the energy to patient tissue along a cone-shaped ablation path, and wherein the waveguide includes a plurality of branches.

23. A device comprising:

a catheter configured to be introduced in proximity to patient tissue and coupled to a generator that generates energy; and at least one steerable beam antenna carried by the catheter that directs the energy along the cone-shaped ablation path, wherein the catheter directs the energy to patient tissue along a cone-shaped ablation path, wherein at least a portion of the patient tissue within the cone-shaped ablation path is ablated, and patient tissue outside of the cone shaped ablation path is not ablated, wherein the catheter includes a plurality of branches, wherein the at least one steerable beam antenna carried is configured to introduce a phase delay to at least one branch of the plurality of branches, and wherein the steerable beam antenna is configured to introduce a phase delay to at least one branch of the plurality of branches by selecting a path length of for the at least one branch.

* * * * *